(12) United States Patent
Scott

(10) Patent No.: US 7,143,638 B1
(45) Date of Patent: Dec. 5, 2006

(54) WET GAS MEASUREMENT SYSTEM

(75) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 148 days.

(21) Appl. No.: 11/045,803

(22) Filed: Jan. 28, 2005

Related U.S. Application Data

(60) Provisional application No. 60/540,382, filed on Jan. 30, 2004.

(51) Int. Cl.
G01N 37/00 (2006.01)

(52) U.S. Cl. .................. 73/61.43; 73/61.41; 73/53.01

(58) Field of Classification Search ............... 73/61.43, 73/61.41, 53.01, 23.2
See application file for complete search history.

(56) References Cited

U.S. PATENT DOCUMENTS 3,735,558 A * 5/1973 Skarstrom et al. ............. 95/51
6,593,753 B1   7/2003 Scott et al. .................. 324/637
6,810,719 B1  11/2004 Dutton et al. ................. 73/61.4
6,831,470 B1 * 12/2004 Xie et al. ..................... 324/693
2003/0215366 A1 * 11/2003 Nowinski et al. ............. 422/80

OTHER PUBLICATIONS

Mehdizadeh, P; Marrelli, J; Ting, Ven; Wet Gas Metering: Trends in Applications and Technical Developments, SPE 77351 (SPE Annual Technical Conference and Exhibition.
In San Antonio, Texas 09/29-10/02/2002; pp. 1-14, Society of Petroleum Engineers Inc.; Richardson, Texas, USA.

* cited by examiner

Primary Examiner—Hezron Williams
Assistant Examiner—Rodney Frank
(74) Attorney, Agent, or Firm—Groover & Holmes

(57) ABSTRACT

A system and method for measuring an amount of constituent elements in a wet gas mixture, particularly of a wet gas containing petrol. As the wet gas is passed through a two stage measurement system, the total permittivity of the mixture and the amount of water in the mixture are determined. These data, combined with some assumptions about the system, permit calculation of the amount of petrol in the mixture.

29 Claims, 11 Drawing Sheets

WET GAS MEASUREMENT SYSTEM

CROSS-REFERENCE TO RELATED APPLICATIONS

This application claims priority from U.S. Provisional Application 60/540,382 filed 30 Jan. 2004, which is hereby incorporated by reference.

BACKGROUND AND SUMMARY OF THE INVENTION

1. Technical Field

The present inventions relate generally to measuring the contents of a mixture, and more specifically to measuring the constituent contents of a wet gas at any point along the gas pipeline where a measurement is required including subsea and onshore.

2. Description of Related Art

Crude oil usually comprises a mixture of elements, often including petrol, water, and various gasses. A determination of constituent contents in crude oil is required to measure accurately net volumes of actual oil in sales, taxation, exchanges, and custody transfers. Tankers are now transporting liquefied products to ports of call, which would also require measurement. Main pipelines are exchanging products between different owners, and therefore, the contents need to be measured. The water content of crude oil is also significant because it can cause corrosion of equipment and problems in processing. Thus, various methods have been developed for measuring the contents of crude oil.

Background: Wet Gas Measurement in Subsea Pipelines

Wet gas metering covers a variety of measurements in production streams with high to very high gas volume fractions. There is a need for the direct measurement of gas under these conditions in such applications as gas condensate and high GOR (gas oil ratio) fields as well as many production operations where gas from separation systems may contain liquid. More gas will be produced in the future from remote and subsea fields where production, capital investment, and operating costs must be optimized. For example, real time measurement of gas and liquid flow rate are critical in a subsea production system, which will improve well allocation, optimize reservoir production, and enhance flow assurance. (SPE 77351, "Wet Gas Metering: Trends in Applications and Technical Developments", Mehdizadeh et al., Society of Petroleum Engineers, Inc., 2002, which is hereby incorporated by reference.)

Offshore lines coming to shore also need to be measured because they are required to have a low water content to prevent hydrate formation in the line.

Background: Standard Wet Gas Flow Meters

The difficulty in measuring wet gas arises from the fact that gas and liquid are both fluids with different properties. In a standard flow meter, the measured pressure of a flowing fluid can be used to determine its velocity, from which its volumetric flow rate is calculated. If the fluid is all gas or all liquid, the differential pressure accurately reflects the flow rate. With a mixture, however, there are no distinctions between the two, which results in uncertain measurement of both fluids. To determine the individual flow rates, the ratio of gas to liquid must be known.

The inaccurate reading is a result of the design of the standard flow meter. The basic flow meter consists of a pipe that is constricted on one end. The constriction causes the fluid flowing through the pipe to accelerate. Before and after the constriction; two pressure measurements of the accelerating liquid are taken and the difference in pressure is converted into a volumetric flow rate.

Background: Aluminum Oxide for Moisture Adsorption

The use of aluminum oxide for moisture adsorption is well known in the industry. The surface attracts and retains water molecules by association with the bonds. Since this is a weak attraction, there is a point at which the absorption and desorption reaches an equilibrium with the surrounding moisture content. Moisture measurements have been made with capacitance measurements using a very thin aluminum oxide surface with imbedded electrodes. When the water is absorbed, the capacitance changes, and therefore, a measurement is made. This surface must be thin in order to allow the water molecules to accumulate in a region where the electrical field is present. This thin region usually has gold or other metal flashed onto the surface to implement a conductivity or capacitance measurement. This metalization also allows contaminants such as ethylene glycol and methanol to become trapped between the metal and the substrate that biases the measurement.

It is well known to electrical engineers generally (and particularly to microwave engineers) that the frequency of an RF (radio frequency) oscillator can be "pulled" (i.e. shifted from the frequency of oscillation which would be seen if the oscillator were coupled to an ideal impedance-matched pure resistance), if the oscillator sees an impedance which is different from the ideal matched impedance. Thus, a varying load impedance may cause the oscillator frequency to shift.

To help explain the use of the load-pull effect in the disclosed innovations, the electromagnetics of a dielectric-loaded transmission line will first be reviewed. If a transmission line is (electrically) loaded with a dielectric material, changes in the composition of the dielectric material may cause electrical changes in the properties of the line. In particular, the impedance of the line, and the phase velocity of wave propagation in the line, may change.

This can be most readily illustrated by first considering propagation of a plane wave in free space. The propagation of a time-harmonic plane wave (of frequency f) in a uniform material will satisfy the reduced wave equation:

$$(\nabla^2 + k^2)E = (\nabla^2 + k^2)H = 0,$$

where

E is the electric field (vector),

H is the magnetic field (vector), and $\nabla^2$ represents the sum of second partial derivatives along the three spatial axes.

This equation can be solved to define the electric field vector E, at any point r and time t, as $$E(r,t) = E_0 \exp[i(k \cdot r - \omega t)],$$

where k is a wave propagation vector which points in the direction of propagation and has a magnitude equal to the wave number k, and $\omega$ = Angular Frequency = $2\pi f$.

In a vacuum, the wave number k has a value "$k_0$" which is $$K_0 = \omega/c$$
$$= \omega(\mu_0 \varepsilon_0)^{1/2},$$

where
- $\rho_0$=Magnetic Permeability of vacuum ($4\pi \times 10^{-7}$ Henrys per meter),
- $\varepsilon_0$=Electric Permittivity of vacuum (($1/36\pi) \times 10^{-9}$ Farads per meter), and
- c=Speed of light=$(\rho_0 \varepsilon_0)^{-1/2}$=$2.998 \times 10^8$ meters/second.

However, in a dielectric material, the wave number k is not equal to $k_0$; instead $$k = \omega/(c(\mu_r \varepsilon_r)^{1/2})$$
$$= \omega(\mu_0 \mu_r \varepsilon_0 \varepsilon_r)^{1/2},$$

where
- $\mu_r$=Relative Permeability of the material (normalized to the permeability $\mu_0$ of a vacuum), and
- $\varepsilon_r$=Relative Permittivity of the material (normalized to the permittivity $\varepsilon_0$ of a vacuum).

Thus, if the relative permeability $\mu_r$ and/or the relative permittivity $\varepsilon_r$ vary, the wave number k and the wave propagation vector k will also vary, and this variation will typically affect the load pulled oscillator frequency.

Frequency Hopping in a Load-Pulled Oscillator

In a typical free-running oscillator, the oscillator frequency is defined by a resonant feedback circuit (the "tank" circuit), and can also be pulled slightly by a reactive load, as noted above. Thus, such an oscillator can be broadly tuned by including a varactor in the tank circuit.

As the oscillator's frequency is thus shifted, the phase difference between the energy incident on and reflected from the load element (which is preferably a shorted transmission line segment) will change. This phase difference will be equal to an exact multiple of 180° at any frequency where the electrical length of the transmission line segment is an exact multiple of $\lambda/4$.

As the oscillator frequency passes through such a frequency (i.e. one where the transmission line segment's electrical length is equal to a multiple of $\lambda/4$), the load's net impedance will change from inductive to capacitive (or vice versa). As this occurs, the frequency of the oscillator may change abruptly rather than smoothly. This jump in frequency will be referred to as a frequency "hop".

For a transmission line of length 1 which contains a dielectric material of relative dielectric constant $\varepsilon_r$, the frequency at which one full wavelength ($1\lambda$) exists in the transmission line is equal to c (the speed of light in vacuum, which is $2.995 \times 10^8$ meters/second) divided by the length of the line in meters and by the square root of the relative dielectric constant of the material:

Frequency$_{1\lambda}$=c/($1_{\varepsilon_r}^{1/2}$).

For example, for a one-foot-long line filled with a material having $\varepsilon_r$=1, l=12 inches (=0.3048 meters), and Frequency$_{1\lambda}$=$(2.995 \times 10^8)/(0.3048 \times 1.0) \approx 980$ MHz.

However, since one wavelength actually contains two excursions from inductive to capacitive reactive impedances, only one-half wavelength is required to see one frequency hop of the load pulled oscillator. If the transmission line is terminated into a short or an open, the resulting effective length is increased to twice the actual length, since a standing wave is generated (due to the energy incident at the short or open being reflected back to the input of the transmission line). In essence, the energy travels down the line, gets reflected, and travels back to the input. With this taken into account, the first frequency with a wavelength long enough to cause a frequency "hop" of the oscillator is one fourth the length calculated above, or 245 MHz.

Multiples of this first quarter-wavelength frequency will also cause the impedance seen at the input to the transmission line to go from inductive to capacitive reactance. The longer the transmission line, the greater the number of phase transitions that will occur. Longer line length also multiplies the phase changes that are brought about by a change in the dielectric constant. For every one-quarter wavelength change in the effective (electrical) length of the line, the complex impedance seen at the oscillator changes by 180°.

For example, suppose that a given oscillator, coupled into a low loss load with an electrical length of one-quarter wavelength ($\lambda/4$), provides typically 50 MHz of load pulling frequency change (total excursion through all phases $-\lambda/4$ would have 180 degrees). If the monitored material changes enough to produce a change of only one degree of phase in the electrical length of the load, the oscillator frequency will change by 50 MHz divided by 180 degrees=277.78 kHz per one degree. This represents an absolute resolution of $3.6 \times 10^{-6}$ degrees of phase change for each Hertz of sensitivity. For every additional quarter wavelength of line length, this sensitivity to phase is multiplied by 1.5. This is due to the change in phase being an additive function of every additional quarter wave in the measurement section.

In a typical tuning frequency versus voltage plot for a VCO (voltage controlled oscillator) loaded into a shorted transmission line, the height of the "hop" can be measured by holding the VCO tuning voltage constant, while a transmission line terminated into a short is varied in electrical length to cause a full rotation of the impedance vector seen at the VCO's input port. The resulting data of frequency versus length of the transmission line will show a jump in frequency (a delta frequency from the bottom of the "hop" to the top of the "hop") which coincides with the delta frequency of the "hop" seen when the VCO was swept using the tuning voltage.

Thus, if the VCO is swept across a frequency band and the number of frequency "hops" was counted, the number of "hops" reveals the number of wavelengths in the transmission line.

This provides a means for determination of the range of dielectric constant change in a medium even when it rotates the phase vector multiple times (and therefore, the oscillator frequency returns to the same value multiple times). If the dielectric constant of the material in the transmission line is increased, then the above equations show that the frequency of the first full wavelength is decreased by the square root of the dielectric constant. Additionally, this means that the number of wavelengths at a fixed frequency increases with increasing dielectric constant. These facts imply that the VCO tuning curve will see more "hops" as the dielectric constant is increased due to the increasing fraction or whole wavelengths encountered.

Ideally, the oscillator will not cease oscillations (or break into multiple frequency oscillation or spectral breakup) into any load regardless of the load characteristics. However, this is not a strictly necessary condition for use of the disclosed method and system innovations.

Measurement of Substances with a High Microwave Loss Factor

A measure of the dielectric loss of a material is typically given as the dielectric loss tangent (a unit-less parameter) which is defined as the tangent of the imaginary part divided by the real part of the complex dielectric constant. Low loss materials are typically below a loss tangent equal to or less than 0.01. When the disclosed systems are used to measure materials with a high loss factor, the material's absorption begins to dominate the load versus frequency effects, but a measurement capability still exists due to the sensitivity of the load pulling method.

Additional information, which can be obtained from conventional microwave measurement methods and also from load pulled measurement, is covered below.

Difference in Operation Frequency

Additional information can be obtained by making another measurement at a much higher frequency. Since materials change properties versus frequency, the amount of frequency change will vary versus the frequency of operation.

A VCO will typically be designed to cover approximately one octave above its turn on frequency. If a VCO would not give enough frequency change to see the desired range of varying parameters versus operating frequency, additional oscillators, which run at any frequency required to obtain appropriate data, can be used and may be switched into the coaxial line.

When two widely spaced frequencies are measured for a medium under study, the difference (delta) frequency between these two measurements will be unique for a given medium. This phenomenon will aid in distinguishing constituents and the progress of mixing or reaction.

Monitoring of Insertion Loss

If the incident power and the reflected power are measured in a system where the final load is a short, the difference in powers will be twice the insertion loss of the medium (since two transits occur through the medium of interest). The insertion loss measurement will aid in determination of the changing conductivity of the medium or its change in absorption of the RF energy. This information can be related to the mixing or reaction products to further distinguish unique situations. Also a transmission measurement can be implemented where the through loss is measured by power incident on the measurement section and after the measurement section. This is through conventional microwave measurement means.

Effect of Complex Permeability

The magnetic permeability $\mu_r$ can also be dynamically measured by the disclosed techniques. Since the velocity varies with $(\mu_r \epsilon_r)^{-1/2}$, changes in $\mu_r$ will change the phase shift through a given physical length of line, and thus change the frequency of the oscillator.

A sample-containing waveguide, like that of the principally preferred embodiment, will typically have locations where the electric field is strong but the magnetic field is zero; at such locations only permittivity will affect the oscillator load pull frequency. However, there will also commonly be locations in a waveguide where the magnetic fields are locally strong and electric field is zero: at these locations, only the permeability will affect the propagation characteristics of the transmission line (and, therefore, contribute to the oscillator frequency for a load pulled oscillator or would contribute to the phase and amplitude measurement of a conventional microwave measurement system).

A system can be built to sample (primarily) one of these parameters. For example, to sample the permeability, the coaxial transmission line will be terminated into a short where the medium of interest is located only in close proximity to the short. A waveguide structure supports very well defined electrical and magnetic field functions, and the sample can be suitably placed in such a structure to measure primarily the permeability.

Typical compounds and substances do not have varying magnetic permeabilities and therefore, most of the discussion will involve the changing complex permittivity. However, the effects of changing complex permeability will create similar changes in the oscillator load pulling characteristics or in the conventional microwave system phase and amplitude. If a substance such as barium titanate is studied, the effect of the changing permeability must be considered along with the change in permittivity unless the system is designed specifically to measure only one of these.

Coupling the Active Device in a Load Pulled Oscillator

An unusual feature of the oscillator configuration used with the present invention is the separation of the load of interest from the resonant circuit proper. The configuration used isolates the two through the active device. It is the non-linear behavior of the transistor that provides the changes in frequency as the load is changed. The loop gain of an oscillator must be unity with an appropriate phase shift to cancel the negative impedance's imaginary part around the resonant loop. The initial gain of the active device must be greater than unity before oscillations can begin in order for the oscillator to be self starting. This extra gain is reduced to unity by the saturation of the active device upon establishment of the oscillations. Saturation of a device normally also changes the phase shift through the device. This requires a change in the operation frequency as the load changes due to the shift in loop gain and phase by the saturated condition change in the active device.

Spectral Purity of Oscillator in a Load Pulled Oscillator

It has been discovered that, in a system using a free-running oscillator as described above, spectral purity of the oscillator is an important concern. Many microwave oscillators exhibit "spectral breakup", wherein the spectrum of the oscillator's output actually contains multiple frequencies. In most microwave oscillators, this is not a problem since a tuned feedback element will be used to stabilize the gain element, and/or isolation or buffering stages are used to prevent the oscillator's feedback loop from being perturbed by extraneous resonances. However, in a load-pulled system, since such buffer stages are not used, spectral purity turns out to be quite important. For example, a spurious resonance in the feedback loop (e.g. due to a low-quality RF choke, or due to two impedance mismatches) can permit the oscillator to hop to a frequency which is determined (at least partly) by a harmonic of the spurious resonance, in which case the degree to which the oscillator frequency has been pulled by the changing load will be obscured.

To avoid such problems in a load-pulled system, a small series resistor can be interposed in the RF output of the oscillator, before the measurement section connection. This resistor adds a small amount of damping, which helps to suppress oscillation at secondary frequencies.

To further improve stability, a shunt resistor can be attached to the RF output of the load-pulled oscillator. This resistor adds to stability, by fixing a maximum magnitude for the load impedance seen at the RF output line.

Background: Other Approaches to Electrical Characterization

Various types of apparatus have been proposed for measuring the concentration of one substance in another, particularly the concentration of a liquid or flowable substance in another liquid or flowable substance. Various devices that utilize the broad concept of determining composition of matter by measuring changes in a microwave signal are disclosed in U.S. Pat. No. 3,498,112 to Howard; U.S. Pat. No. 3,693,079 to Walker; U.S. Pat. No. 4,206,399 to Fitzky et al.; U.S. Pat. No. 4,311,957 to Hewitt et al.; U.S. Pat. No. 4,361,801 to Meyer et al.; U.S. Pat. No. 4,240,028 to Davis Jr.; U.S. Pat. No. 4,352,288 to Paap et al.; U.S. Pat. No. 4,499,418 to Helms et al.; and U.S. Pat. No. 4,367,440 and U.S. Pat. No. 4,429,273, both to Mazzagatti; all of which are hereby incorporated by reference.

U.S. Pat. No. 6,593,753 to Scott et al. teaches a planar probe with two transmission lines. However, this particular innovation detects the differences in chemical interactions and is directed towards characterizing a single phase (such as an all liquid stream) stream. It is not designed to measure a multi-phase stream such as wet gas (moisture in gas, natural gas, natural gas liquids and free water) and does not take into account factors such as the pressure and temperature of the substance being measured, which become important in multiphase stream analysis. This particular innovation was also designed to be used with a load-pulled oscillator. By contrast, the present inventions disclose methods and systems for determining the amount of water, petrol, and gas in a multi-phase, wet gas stream. This determination can be made with any standard microwave method and is not limited to load-pulled oscillators.

U.S. Pat. No. 6,810,719 to Dutton et. al. relates to a flow measurement system that comprises a separator, a Coriolis flow meter, and a water cut monitor. This patent also appears to employ calculations that require iterative solutions. The method disclosed herein provides an additional variable by which the solution for the equations is simplified greatly. Also by contrast, the present innovations do not require a separator or flow meter although a Coriolis flow meter providing density to aid in the solution of the equations would be beneficial. Typically, Coriolis flow meters cease working at some point when the flowing medium of gas and liquids becomes non-homogeneous. The present innovations also provide a method for calculating the amount of petrol, water, and gas in a wet gas that is less computationally intensive than U.S. Pat. No. 6,810,719.

Wet Gas Measurement System

The present inventions relate to measuring the constituent contents of a wet gas. It is preferably implemented at any point along the gas pipeline where a measurement is required including subsea and onshore.

The present inventions determine the total permittivity of a wet gas and the amount of water in the wet gas. These data, combined with some assumptions about the system, permit calculation of the amount of petrol in the mixture.

In one preferred embodiment, the present inventions comprise two independent probes for identifying the amount of petrol, water, and gas in a wet gas. The probes each have one or more openings that allow the materials of the flow to penetrate and enter the probes.

The first probe allows passage of the flow of the mixture into the chamber of the probe. The permittivity of the mixture inside the chamber of the probe is measured. This probe provides the overall permittivity of the entire mixture.

The second probe, preferably immediately downstream of the first probe, is configured with a microwave system and includes aluminum oxide or similar bed of material so that the total water content of the flow is measured. The aluminum oxide or similar material is chosen so that it attracts and holds water in proportion to the water content in the flow. As the moisture content in the flow changes, the proportion of water inside the probe, and hence the measured permittivity, will change. Thus, the second probe filled with alumina or other material provides understanding of the permittivity of the water portion of the mixture in the flow.

This information, combined with the overall permittivity of the gas, oil, and water as obtained from the first probe, allows for the determination of the amount of petrol and the amount of gas in the wet gas mixture.

BRIEF DESCRIPTION OF THE DRAWINGS

The novel features believed characteristic of the inventions are set forth in the appended claims. The inventions themselves, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1A:
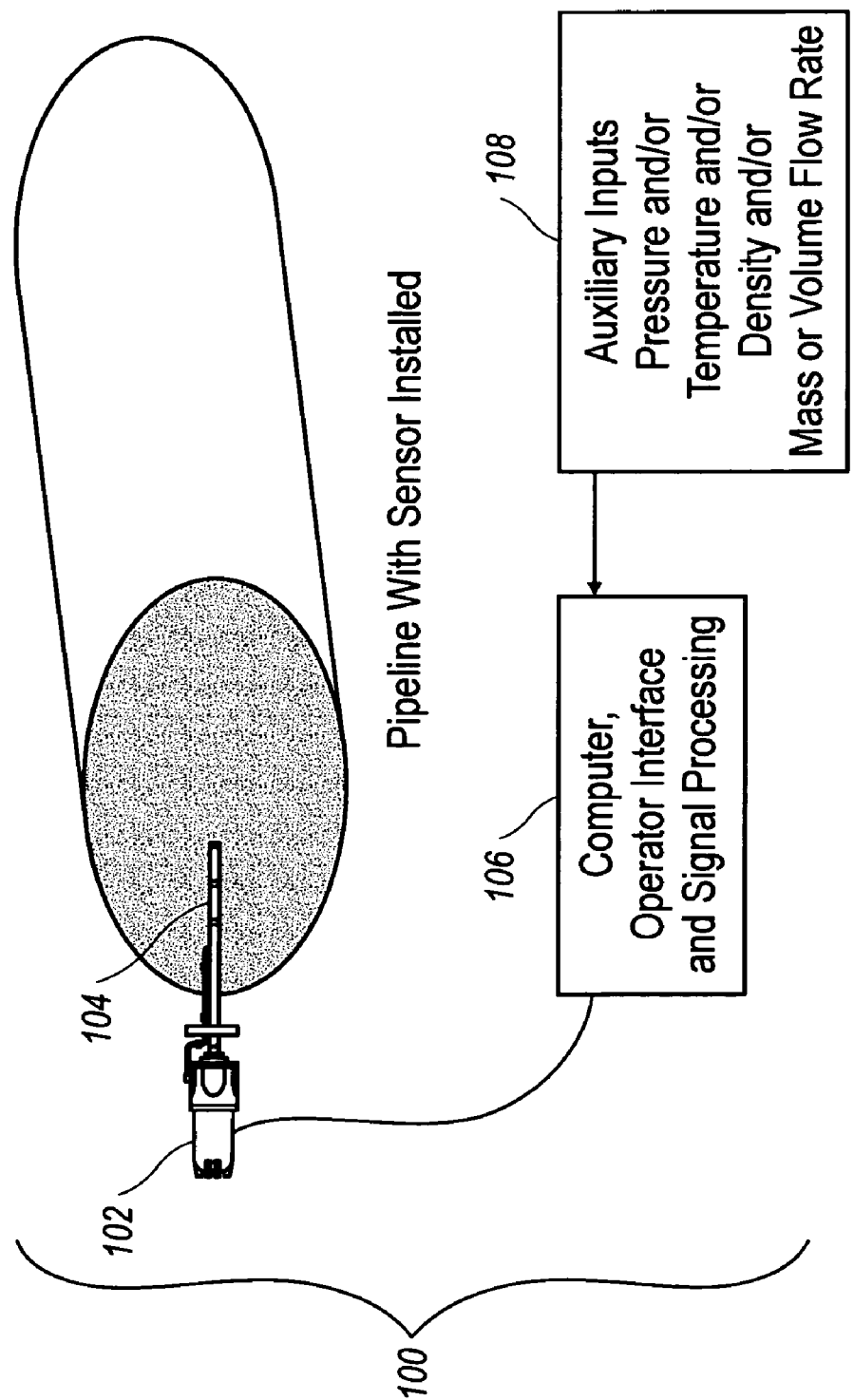
FIG. 1A shows a general embodiment of a testing apparatus of the present inventions.
Figure 1B:
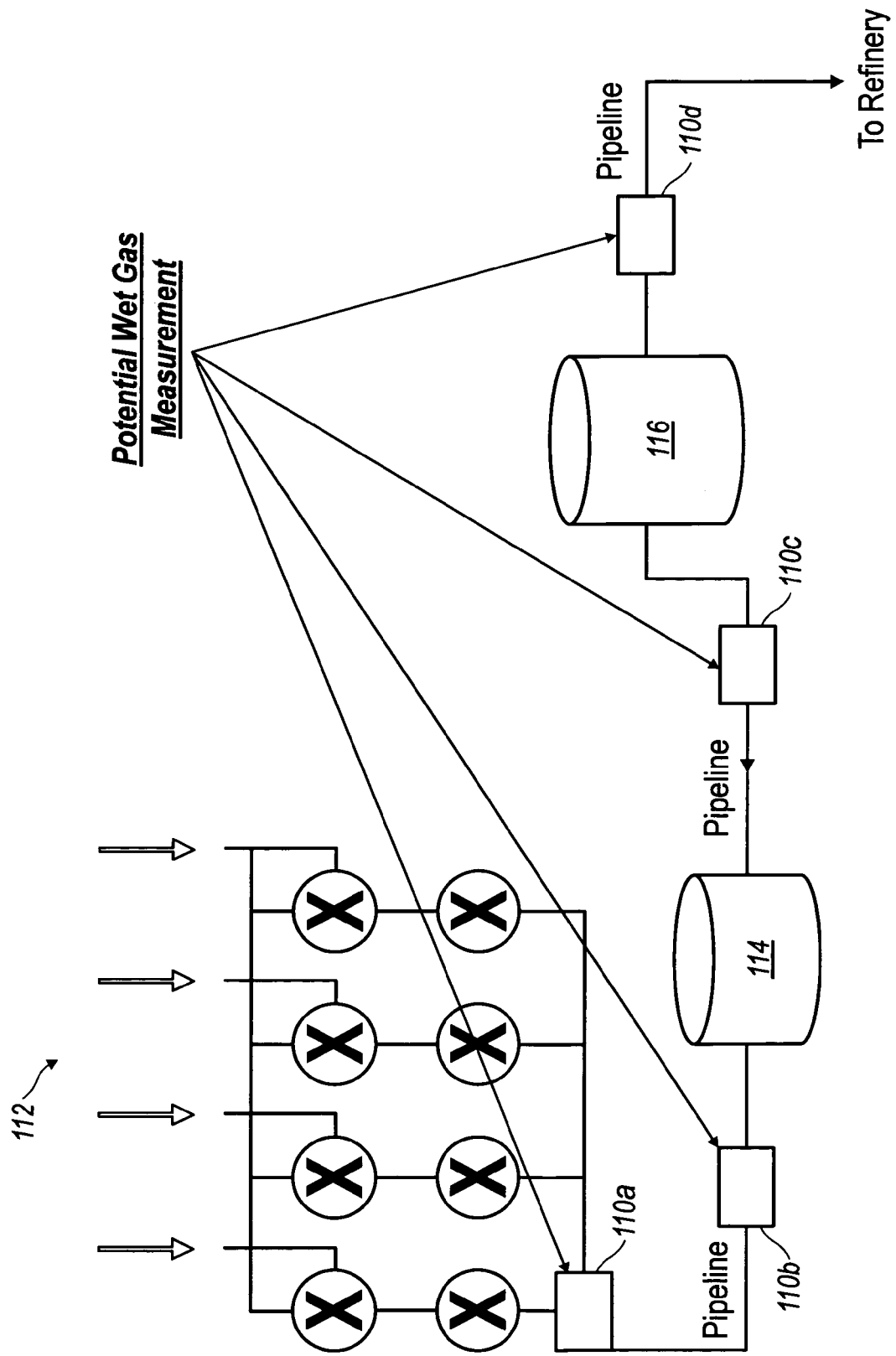
FIG. 1B shows an example of the various places along a gas production pipeline where a testing apparatus of the present inventions may be incorporated into a pipeline.

FIGS. 1A and 1B show a pipeline and testing apparatus consistent with implementing a preferred embodiment of the present inventions. It is noted that FIGS. 1A and 1B are only intended to show one context in which the present innovations may be implemented, and is not intended to limit application of the innovations herein disclosed.

FIG. 1A shows a general embodiment of a testing apparatus of the present inventions. In this particular embodiment, testing apparatus 100 is shown with a source 102 and probe 104. A computer 106 is used for signal processing. Auxiliary inputs 108 are used to provide information, such as pressure, temperature, density, mass, and/or volume flow rate, to computer 106. These additional parameters are used to mathematically correct for given line conditions of the gas and liquids to refer them back to standard temperature and pressures (one atmosphere 60° F.) as the industry requires.

FIG. 1B shows an example of the various places along a gas production pipeline where a testing apparatus, such as testing apparatus 100, of the present inventions may be incorporated into the pipeline. In this particular embodiment, a testing apparatus of the present inventions may be incorporated into the gas production pipeline at various places. For example, a testing apparatus may be incorporated at points 110a and 110b between wells 112 and slug catcher 114. (Wells 112 may be topside or subsea.) A testing apparatus may also be incorporated at a point 110c between slug catcher 114 and storage or dehydration section 116. A testing apparatus may also be incorporated at a point 110d between storage or dehydration section 116 and the refinery.

Figure 2:
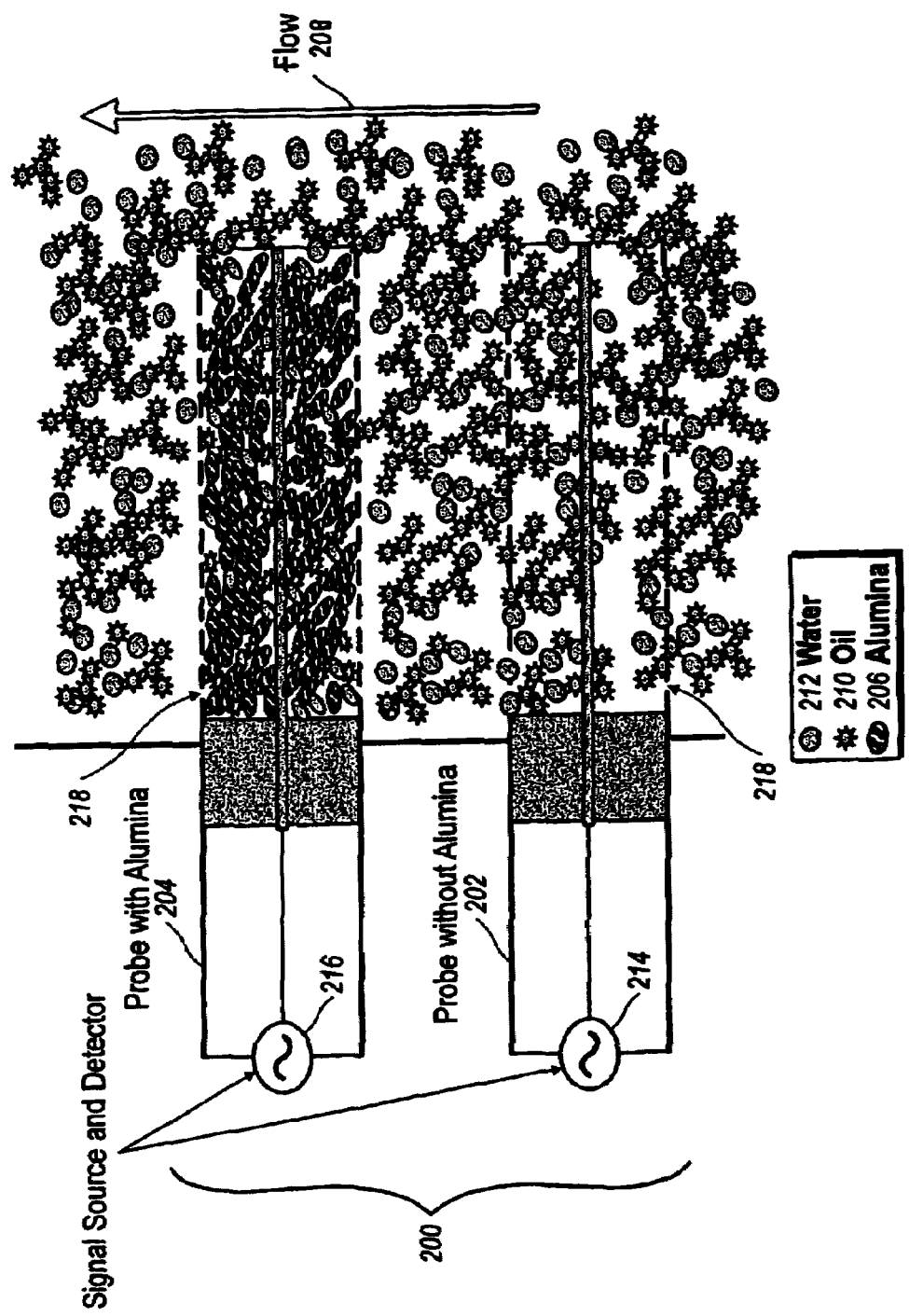
FIG. 2 shows two independent probes in a wet gas flow consistent with implementing a preferred embodiment of the present inventions.

FIG. 2 shows an innovative system 200 with two independent measurement stages, implemented here as probes 202, 204 implemented consistent with a preferred embodiment of the present inventions. In this example, a first probe 202 having an empty coaxial line and a second probe 204 with alumina 206 are inserted into flow 208 of a pipeline or other source. In preferred embodiments, the flow includes petrol 210, gas, and water 212. In one example embodiment, the probes 202, 204 each have one or more openings 218 that allow the materials of flow 208 to penetrate and enter probes 202, 204. Although alumina is a preferred hydrophilic material, any type of desiccant such as molecular sieves, polyacrylic acid, silica gel, calcium oxide, calcium sulfate, and clay desiccant may be used.

In a preferred implementation, the wet gas including petroleum and water are mixed so that the liquid is well dispersed in the gas. This mixing can occur from the natural turbulence in the flow apparatus, or other means can be implemented to encourage mixing, such as agitation of the flow before it reaches testing apparatus 200.

The first probe 202 allows passage of the flow of the mixture into the chamber of the probe. The permittivity of the mixture is measured using, for example, the load pull effect of a microwave resonance chamber wherein the probe chamber acts as a transmission line loaded with a dielectric material (i.e., the mixture). Changes in the composition of the dielectric material cause changes in the electrical properties of the line. These changes are detected using signal source and detector 214 with respect to probe 202 (and source and detector 216 with respect to probe 204). These measurements are proportional to the permittivity of the medium although an actual permittivity determination is not required.

A conventional microwave system such as a Hewlett Packard 8410 microwave vector analysis system can be used to determine the scattering parameters for a microwave system with the appropriate design of the probes in the line. This system would give the conventional microwave properties such as reflection coefficient and transmission loss through the probe, which will be relational to the changes with respect to moisture and permittivity.

The second probe 204, preferably immediately downstream of the first probe 202, is configured with a microwave system and includes aluminum oxide or similar bed of material so that the total water content of the flow is measured. The aluminum oxide or similar material 206 is chosen so that it attracts and holds water 212 in proportion to the water content in the flow. As the moisture content in the flow changes, the proportion of water inside the probe 204, and hence the measured permittivity, will change. This change is detected by signal source and detector 216 so that the microwave measurement becomes a mass measurement of the number of captured water molecules in material 206. Thus, the second probe 204 filled with alumina or other material provides understanding of the permittivity of primarily the water portion of the mixture in flow 208. While the second probe 204 measures the permittivity of only the water portion, it is partially affected by the mass of the total production stream flowing through it.

This information, combined with the overall permittivity of the gas, oil, and water as obtained from the first probe 202, allows for further calculations as described below.

Since both measurements are based on the same physics where gas is approximately a dielectric constant of 1.00XX and light petroleum (c12 and less) is approximately 2.2 and water is 68–80 depending on temperature, the approximate total percent of the mix can be characterized as:

$$\text{water \%} + \text{petrol \%} + \text{gas \%} = 1.0$$

which leads to the following relationship:

$$\text{petrol \%} = 1.0 - \text{water \%} - \text{gas \%}$$

Another useful relationship, incorporating the permittivity of each involved substance, is stated as:

$$\text{water \%} \times \epsilon_{water} + \text{petrol \%} \times \epsilon_{petrol} + \text{gas \%} \times \epsilon_{gas} = 1.0 \times \epsilon_{mix}.$$

This equation would be known as a permittivity mixture equation. Through the years, many different research programs have produced various mixture equations for two and three phase mixtures. Other equations can be used, and this simplified one above does not limit the equation types that could be used to define the mixture permittivity.

In preferred embodiments, the percentage of water is found using a second $Al_2O_3$ system, namely, probe 204. Further, the value for $\epsilon_{mix}$ is also known from the probe system, namely probe 202 as shown in FIG. 2.

Next, the dielectric constant of the petrol, gas, and water are estimated, using a measured value of temperature where useful, such as in the case of water. For example, an estimate of the petrol dielectric constant is 2.1 and an estimate of the dielectric constant of the gas, which should be close to unity, is 1.001. Substituting these estimates into the above equations allows measurement of the total percentages of petrol and gas in the mixture.

Permittivity can be expressed as a vector relationship equivalent to the real part being the dielectric interactions of the polar moment and the imaginary portion to the electrical, rotational, and interfacial polarization loss. Although the dielectric constant (a unit-less parameter) was used in the above statements, one can see that the full permittivity can easily be incorporated. Since in a gaseous stream the loss factor should be small, the solution is reduced to just the changes in polar moment or the dielectric constant.

As described above, the two analyzers provide the permittivity of the mix and the amount of water. The permittivity of the petroleum in gas wells does not vary significantly, and the permittivity of the gas should be near unity. The calculations described above also depend on the homogeneity of the mixture. As the droplet size increases and becomes less defined, the accuracy of measurements may suffer. However, most gas wells are above 90% gas by volume percent, and therefore, if the flow rate is significant, turbulence will exist across the devices, and the resulting measurements should be reasonable.

Though FIG. 2 shows two individual sources and measurement systems, the device can also be implemented in other ways, for example, as two coaxial insertable sections that share a single set of electronics, and where the microwave measurement is switched between the two devices. This and further example implementations are discussed further below.

Figure 3:
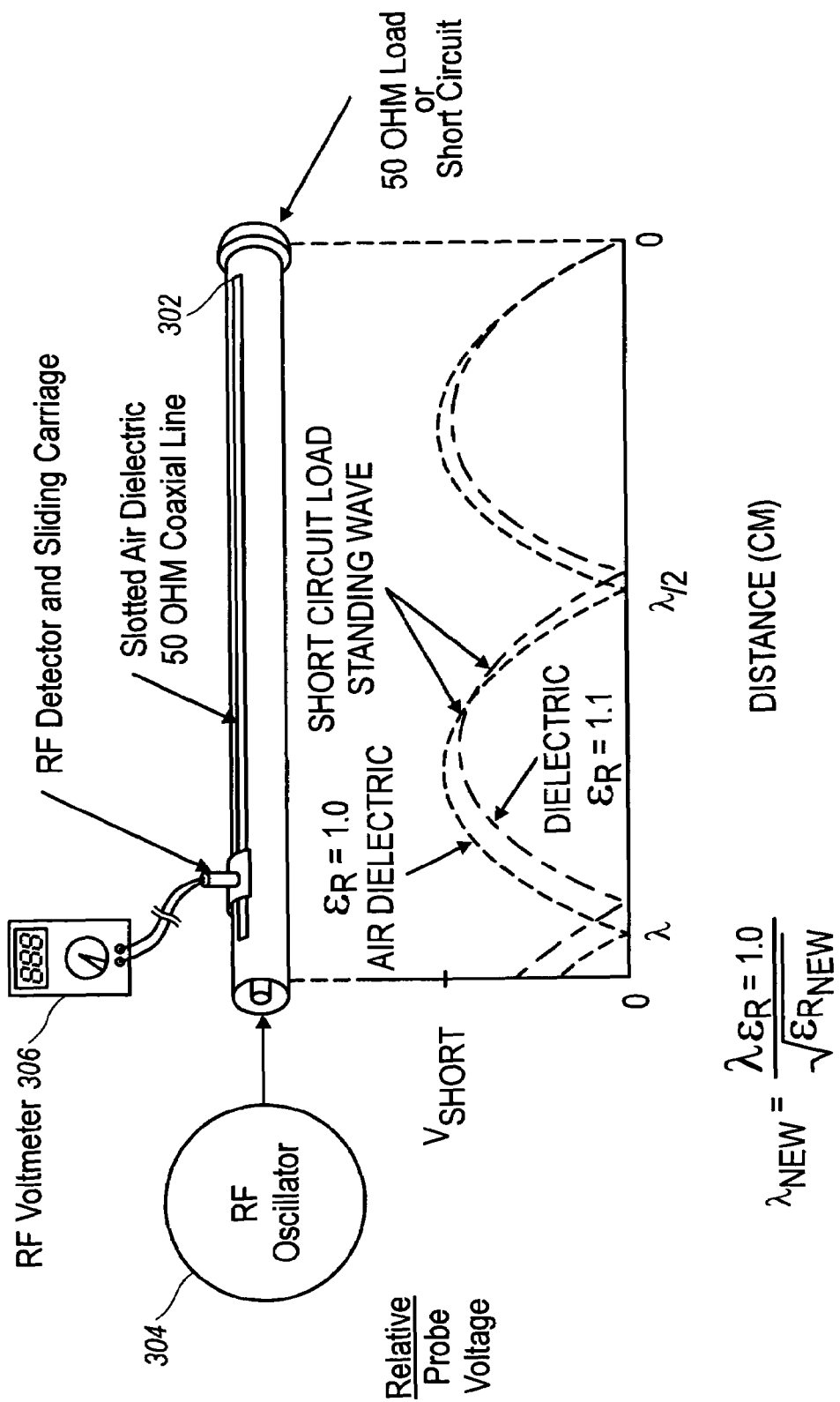
FIG. 3 shows the effect of permittivity differences on a standing wave in a waveguide.

FIG. 3 shows a chart plotting the effects of changing permittivity on a microwave inside the chamber. The chamber 302 acts as a waveguide or resonating chamber for microwaves (or other emissions from RF oscillator 304) and is represented in the graph by the two dashed or broken lines. It is noted that in FIG. 3, the wavelength for the two different dielectric cases (namely dielectrics respectively of 1.0 for air and 1.1 for another substance) changes as the dielectric changes. This change is detected, for example, at RF voltmeter 306. This basic mechanism is implemented, for example, as part of the probe system described in FIG. 2 and further described in the alternative embodiments presented below.

Figure 4:
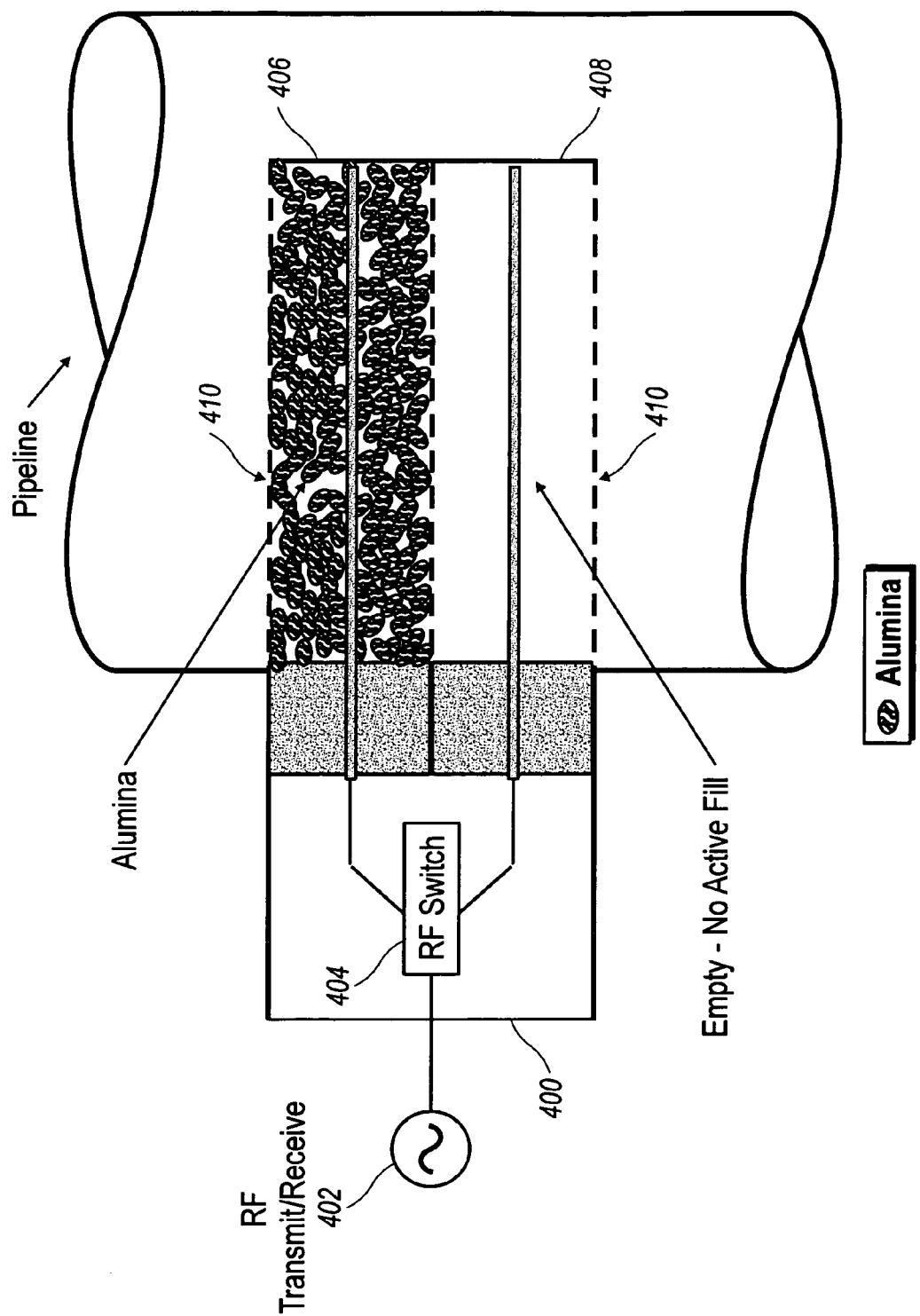
FIG. 4 shows a dual probe and single RF transmit/receive unit consistent with implementing a preferred embodiment of the present inventions.

FIG. 4 shows an implementation of the present innovations using a dual probe system 400 with a single RF transmit/receive 402 and switch 404. In this example, switch 404 switches the signal between the two sections 406, 408 of system 400. In this example, section 408 is open and allows all parts of the mixture in the pipeline to flow through, while section 406 includes alumina, similar to the system described in FIG. 2. In this example, the two chambers are parallel. Switch 404 switches between the two sections, for example, first measuring the electrical characteristics of the mixture in section 408, then measuring the amount of water in the system in section 406. In this example, system 400 includes holes 410 in the sections 406, 408 for the mixture to pass through.

Figure 5:
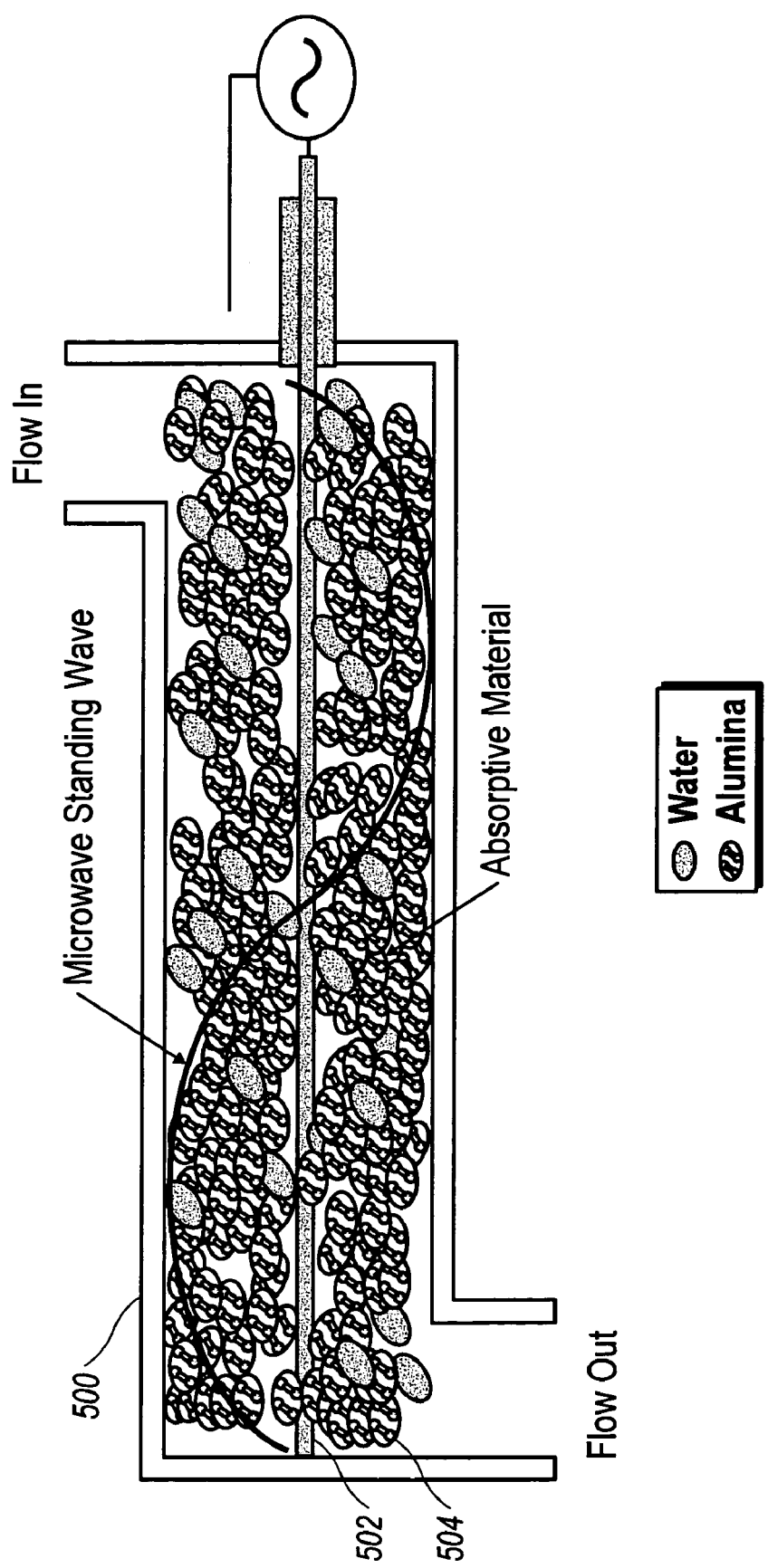
FIG. 5 shows a microwave standing wave in a flow through system, consistent with implementing a preferred embodiment of the present inventions.
Figure 6:
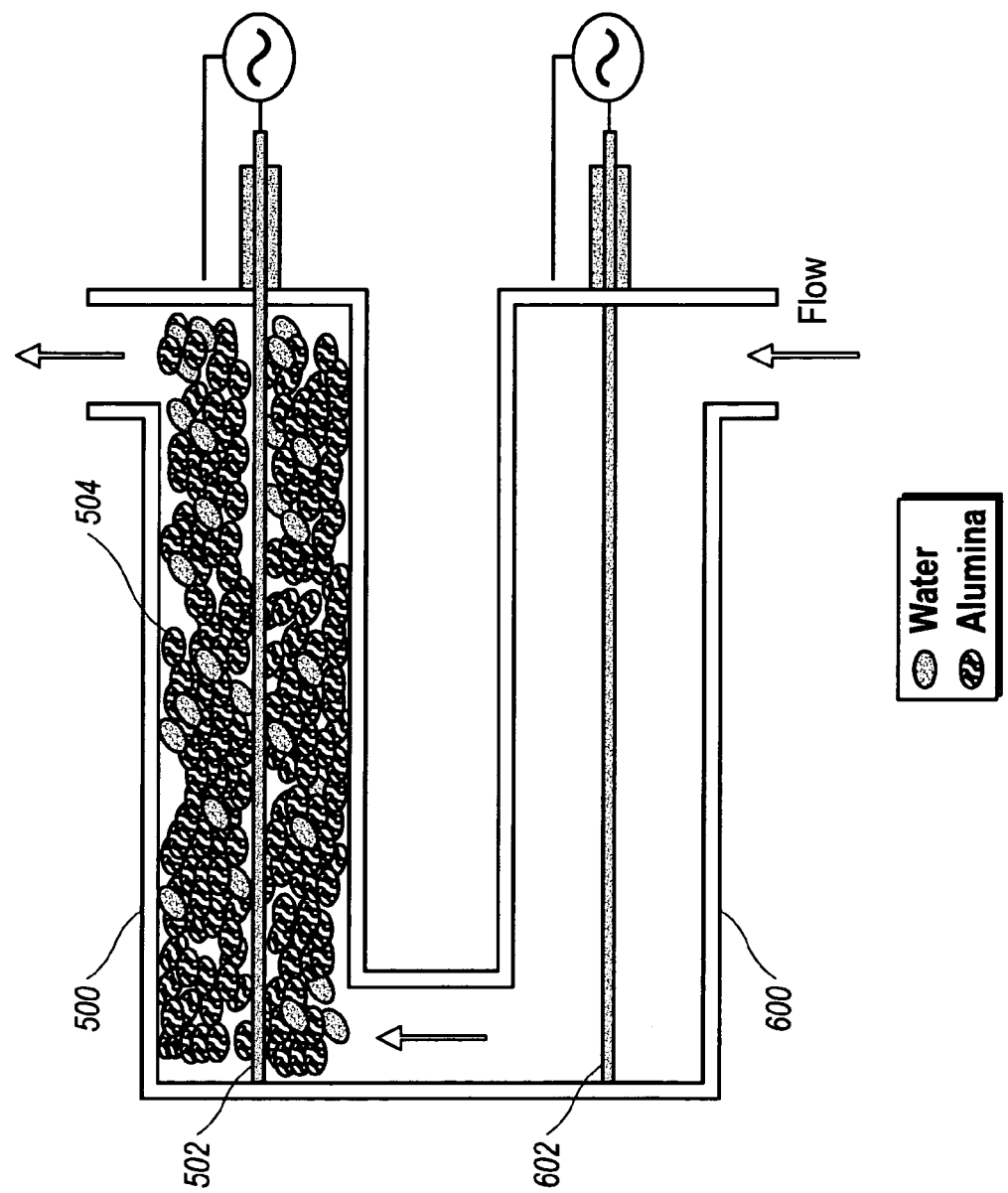
FIG. 6 shows two flow through sections with two signal detectors consistent with implementing a preferred embodiment of the present inventions.

FIGS. 5 and 6 show another embodiment of the present innovations. In this example implementation, a "flow through" system is implemented that does not include the permeable chambers of the prior examples, and which places the two measurement stages in series. In this example, FIG. 5 shows a flow through chamber 500 suitable for implementing in a preferred embodiment of the present inventions. Chamber 500 includes an input and an output through which the mixture of the flow passes. Inside this chamber is a coaxial cable 502 and an amount of absorptive material 504 as described above, such as alumina. This chamber is analogous to chamber 204 of FIG. 2 in that it measures the amount of water proportionally in the mixture.

FIG. 6 shows the chamber 500 in a larger context, including chamber 600 which is analogous to probe 202 of FIG. 2. Chamber 600 includes no alumina or other absorptive material, and is used to measure the electrical characteristics (and thereby the permittivity) of the entire mixture by means of coaxial cable 602 and microwave measurement system as described above. In this example, two separate RF sources and detectors are present, though they could be combined as in the example implementation of FIG. 4. The system shown in FIG. 6 could be inserted directly into a flow path, or it could be part of a diversion from the main flow stream that shunts off a portion of the flow, passes that portion through the test apparatus of FIG. 6, and returns it to the main flow, for example. Other implementations are possible, and these examples are not intended to list an exclusive number of embodiments of the present innovations.

Although the wave guide structure in the above embodiments is described in terms of a coaxial line, any wave guide structure with or without a center conductor may be used to guide the electromagnetic wave.

Figure 7:
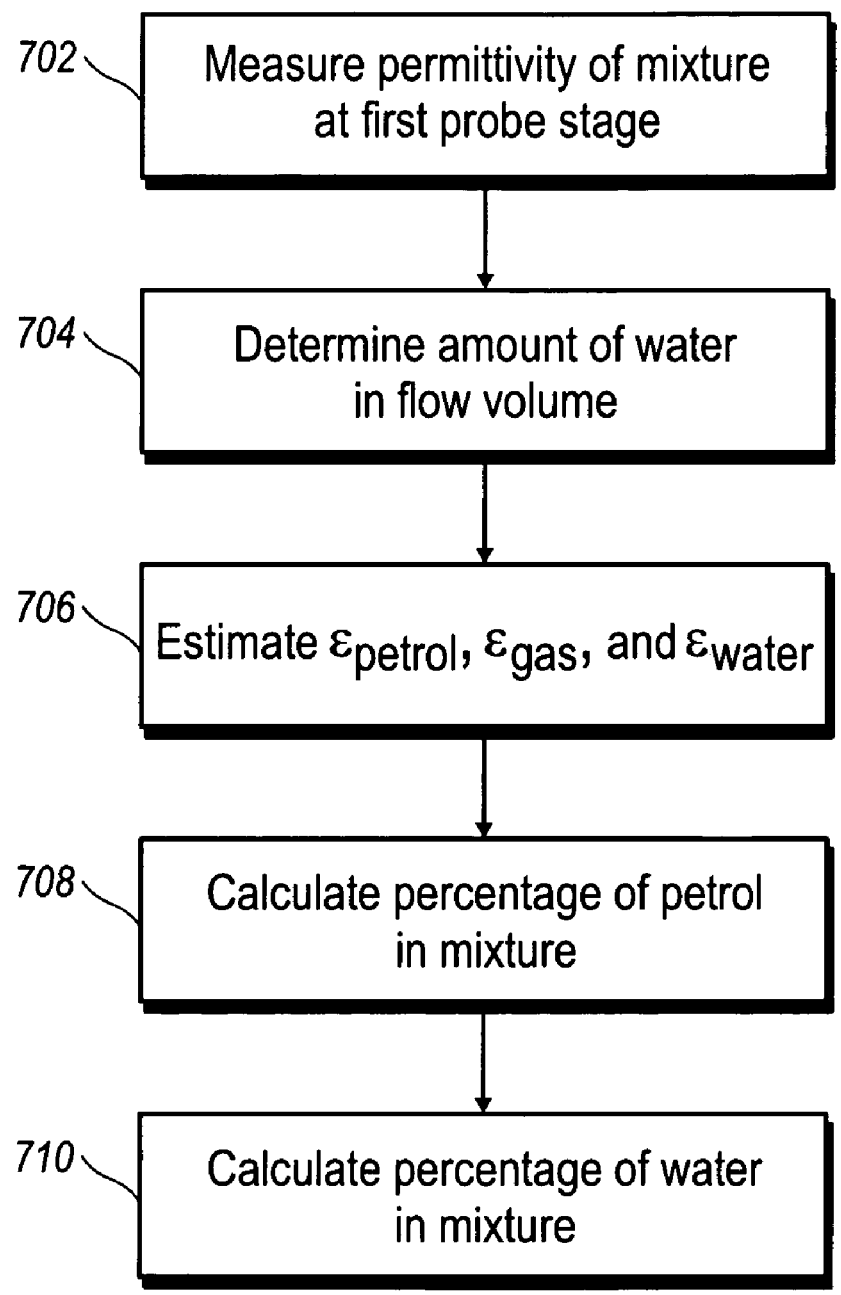
FIG. 7 shows a flowchart with process steps consistent with implementing a preferred embodiment of the present inventions.

FIG. 7 shows a flowchart with process steps for implementing a preferred embodiment of the present innovations. First, the permittivity of the mixture is measured at a first probe (step 702). Second, the amount of water in the system is determined at a second probe, preferably including an alumina (step 704). Estimates of the permittivity of the petrol in the flow, the permittivity of the wet gas in the flow, and of the water in the flow (based on temperature, preferably) are made or obtained (step 706). These data are used to calculate a percentage of petrol in the mixture (step 708) and the percentage of wet gas in the mixture (step 710).

Figure 8:
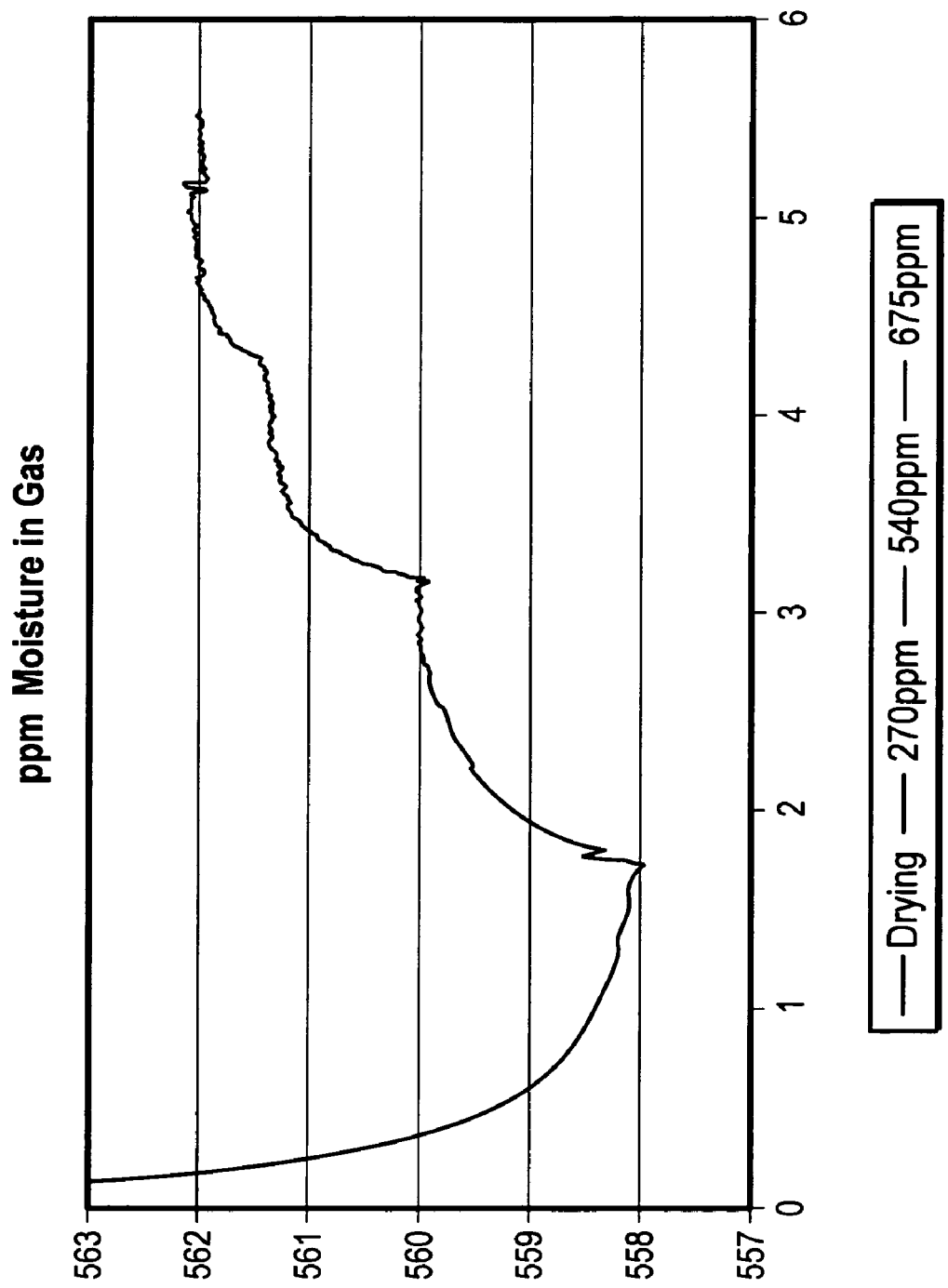
FIG. 8 is a chart of microwave measurement results of activated alumina with known water contents.

FIG. 8 is an example of a chart of microwave measurement results of activated alumina with known water contents. The microwave measurement results from the second probe will be compared against results such as these to determine the water content of the wet gas.

Another implementation of this system is to use a density measurement by other means (such as Coriolis flow meters) to provide additional information to satisfy the solution of N equations and N unknowns. The independent Coriolis density measurement is similar to the first probe measuring the overall permittivity of the flowing mixture. Permittivity is actually the polar moment of the molecules and their loss at microwave frequencies of a mass being measured. The density measurement using Coriolis flow meters is a physical density measurement obtained by measuring the dampening of the vibration of the tubes that the mix is flowing through. This partial redundancy of measurement will provide more accurate solutions for the actual water, liquid petroleum, and gas calculations.

Figure 9A:
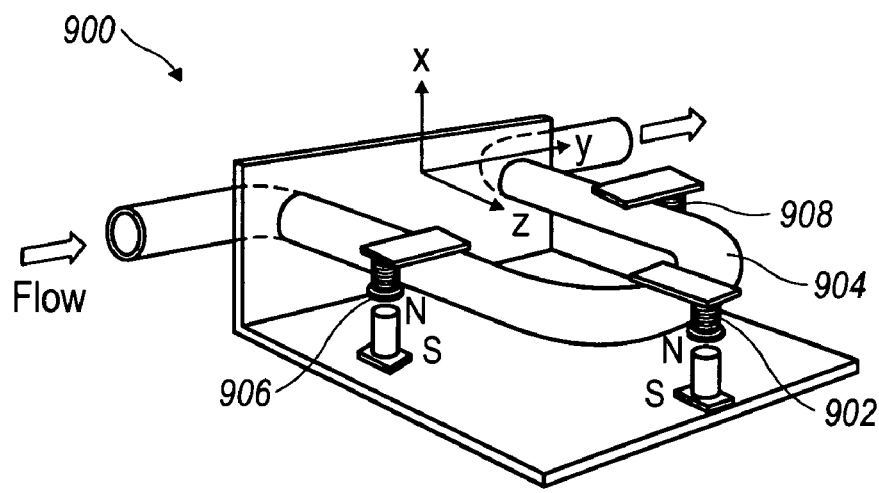
FIGS. 9A and 9B are general depictions of a Coriolis flow meter.
Figure 9B:
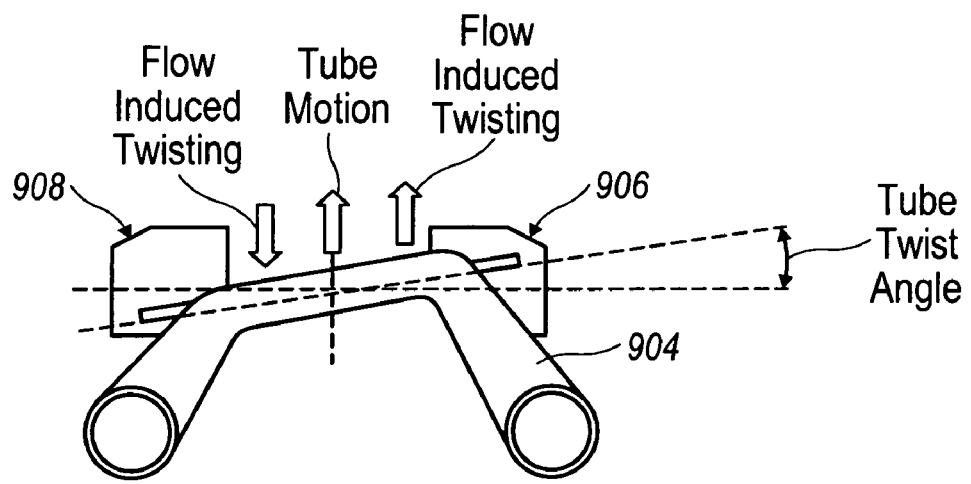

FIGS. 9A and 9B are general depictions of a Coriolis flow meter. In flow meter 900, electromagnetic driver 902 imparts vibrational energy to cause tube 904 to perform a mechanical oscillatory rotation about the y-axis at the tube's fundamental frequency. A feedback circuit maintains the vibration at the tube's fundamental frequency and at a constant amplitude. This feedback circuit uses the amplified signal from either electromagnetic detector 906 or 908 as its input. Fluid flows in opposite directions in the two straight sections and of tube 904 to cause an oscillatory twisting of tube 904 about the y-axis, but it causes a slight difference in the phase between electromagnetic detectors 906 and 908. This slight phase difference is detected and amplified by electronics and is proportional to the mass flowrate of the fluid through the tube.

Although a Coriolis flow meter is shown in FIGS. 9A and 9B, any means of measuring the density of the gas, such as by ultrasonic measurement, may be used.

As stated earlier, the use of a densitometer may be used to provide a redundant estimate of the overall permittivity of a flow.

Alternatively, in another embodiment, a densitometer may be used in place of the first probe. In such an embodiment, the overall density of the flow, obtained from a densitometer, would be used to estimate the overall permittivity of the flow. A probe containing aluminum oxide or similar bed of material would then be used to determine the total water content of the flow as described above.

As stated earlier, flow meter-based, wet gas measuring systems may be used to estimate the density and other fluid/gas properties of a wet gas. In yet another embodiment, the second probe, containing the absorptive material, may be used with one or more flow meter-based, measuring systems, such as an orifice, a Venturi, a vortex, a turbine, or a V-Cone measuring system. The addition of the second probe will provide such systems with one less property to estimate, i.e. the percentage of water in the wet gas. Accordingly, this direct measurement of the percentage of water in the wet gas will improve the measurement of the component percentages of gas, water, and oil estimated by such systems.

Figure 10:
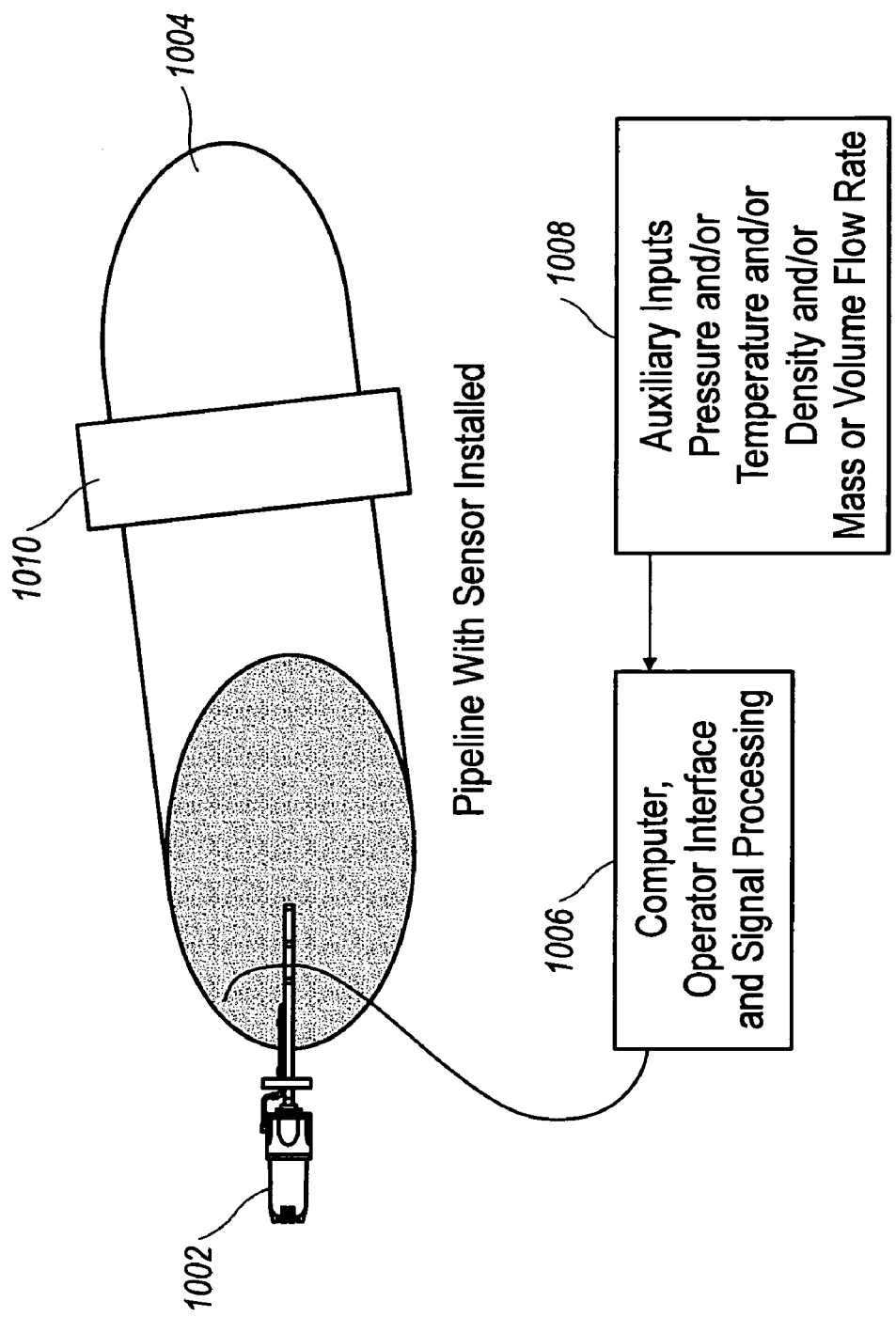
FIG. 10 shows a general embodiment of a probe containing aluminum oxide or similar bed of material used in conjunction with a wet gas measuring system.

FIG. 10 shows a general embodiment of a probe containing aluminum oxide or similar bed of material used in conjunction with a wet gas measuring system. In this particular embodiment, a probe 1002 containing aluminum oxide or similar bed of material is incorporated into pipeline 1004. A computer 1006 is used for signal processing. Auxiliary inputs 1008 are used to provide information such as pressure, temperature, density, mass, and/or volume flow rate to computer 1006. These additional parameters are used to mathematically correct for given line conditions of the gas and liquids to refer them back to standard temperature and pressures (one atmosphere 60° F.) as the industry requires.

Independent system 1010 is used to measure one or more fluid/gas properties of the wet gas flowing through pipeline 1004. Independent system 1010 can be any type of system that measures a property of the wet gas. For example, it can be a densitometer or a flow meter-based, wet gas measuring system, such as an orifice, a Venturi, a vortex, a turbine, or a V-Cone measuring system.

The description of the present inventions has been presented for purposes of illustration and description, but is not intended to be exhaustive or limited to the inventions in the form disclosed. Many modifications and variations will be apparent to those of ordinary skill in the art. The embodiment was chosen and described in order to best explain the principles of the inventions, the practical application, and to enable others of ordinary skill in the art to understand the inventions for various embodiments with various modifications as are suited to the particular use contemplated.

According to a disclosed class of innovative embodiments, there is provided: A wet gas measurement system, comprising: a wet gas; a first measurement stage; a second measurement stage having an absorptive material therein; and an electrical characterization device; wherein the electrical characterization device characterizes a property of the wet gas in at least one of the first or second measurement stages.

According to a disclosed class of innovative embodiments, there is provided: A measurement system, comprising: a passage for a flow of a wet gas; a first probe capable of measuring a characteristic of a material therein; and a second probe filled with a hydrophilic material; wherein as the wet gas passes through the first probe, data associated with the permittivity of the wet gas is measured; and wherein as the wet gas passes through the second probe, water is retained by the hydrophilic material and data associated with an amount of water in the wet gas is measured.

According to a disclosed class of innovative embodiments, there is provided: A method of characterizing constituents of a wet gas, comprising: taking measurements to characterize an overall permittivity of the wet gas; taking measurements to characterize an amount of water in the wet gas; characterizing permittivity of at least one constituent of the wet gas; and calculating a percentage of petrol in the wet gas.

According to a disclosed class of innovative embodiments, there is provided: A method of characterizing constituents of a wet gas, comprising: measuring data associated with permittivity of the wet gas at a first measurement stage; measuring data associated with an amount of water in the wet gas at a second measurement stage; estimating permittivities of constituents of the wet gas; and calculating a percentage petrol in the wet gas.

Definitions

Following are short definitions of the usual meanings of some of the technical terms which are used in the present application. (However, those of ordinary skill will recognize whether the context requires a different meaning.) Additional definitions can be found in the standard technical dictionaries and journals.

The term "wet gas" is used to encompass any gas that contains some liquids and moisture as droplets or liquid in other states. Wet gas has been identified in the literature as being complex to define due to the various pressure, density, and temperature relationships of the mostly gas mixture. The earlier referenced document on this topic should be used as a guideline.

Modifications and Variations

As will be recognized by those skilled in the art, the innovative concepts described in the present application can be modified and varied over a tremendous range of applications, and accordingly the scope of patented subject matter is not limited by any of the specific exemplary teachings given. Some contemplated modifications and variations are listed below, but this brief list does not imply that any other embodiments or modifications are or are not foreseen or foreseeable.

In preferred embodiments, the present invention uses an oscillator system, such as an electrical oscillator system, and more specifically a microwave oscillator system. The exact frequency range of the oscillator can vary from implementation to implementation, and the examples given herein of a microwave oscillator are not intended to limit the invention to only those frequencies. Other frequencies that suitably interact with a sample in such a way that changes in the signal can be detected, such as by measuring scattering parameters. For example, in a load pulled system, the frequency of the oscillator is affected by the sample, which changes the frequency at which the oscillator oscillates. Alternately, transmitted, reflected, and/or incident waves can be affected by the probed material and detected. In such examples, the permittivity of the system seen by the oscillator changes when the sample is introduced, and this change is detected via measuring the scattering parameters, for example. Though we herein characterize the change in the tested system as a change in permittivity, other characterizations are also possible and within the scope of the present invention.

In yet another embodiment, a "patch probe" is implemented, having only a surface area of desiccant material exposed to absorb water from a tested wet gas.

In an embodiment of the present innovations, if the water content of the gaseous portion of the flow is being determined, then the natural turbulence of the gas as it flows through the pipes is enough to ensure a homogenous mixture. The requirement for homogeneity is dependent upon the location of the analyzer. If, for example, the total water content of a 36-inch line is being determined and the analyzer only extends into the line by 6 inches, then the flow must be mixed using, for example, a static mixture to ensure a homogenous mixture. By contrast, if high flow rates are present and the mounting is in the center ⅓ of the diameter of the pipe, homogeneity would probably not be a problem.

None of the descriptions in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A wet gas measurement system, comprising:
   a wet gas;
   a first measurement stage;
   a second measurement stage having an absorptive material therein; and
   an electrical characterization device;
   wherein the electrical characterization device characterizes a property of the wet gas in at least one of the first or second measurement stages.

2. The system of claim 1, wherein the wet gas contains at least petrol, a gas, and water.

3. The system of claim 1, wherein the absorptive material is $Al_2O_3$.

4. The system of claim 1, wherein the wet gas is passed into the first and second measurement stages.

5. The system of claim 1, wherein the electrical characterization device comprises a microwave source and detector.

6. The system of claim 1, wherein the first measurement stage and the second measurement stage comprise chambers which are insertable into a flow path of the wet gas.

7. The system of claim 1, wherein the first measurement state and the second measurement stage comprise chambers connected in series.

8. The system of claim 1, wherein the first and second measurement stages comprise chambers arranged in a roughly parallel fashion such that the wet gas flows through or around both chambers.

9. The system of claim 1, wherein the first and second measurement stages include holes therein which allow passage of the wet gas.

10. The system of claim 1, wherein the electrical characterization device uses load-pulled frequency measurement.

11. The system of claim 1, wherein the first measurement stage comprises a densitometer.

12. The system of claim 1, wherein the first measurement stage comprises a wet gas flow meter.

13. The system of claim 1, wherein the first measurement stage is selected from the group consisting of orifice meter, Venturi meter, vortex meter, turbine meter, and V-Cone meter.

14. A measurement system, comprising:
    a passage for a flow of a wet gas;
    a first probe capable of measuring a characteristic of a material therein; and
    a second probe filled with a hydrophilic material;
    wherein as the wet gas passes through the first probe, data associated with the permittivity of the wet gas is measured; and
    wherein as the wet gas passes through the second probe, water is retained by the hydrophilic material and data associated with an amount of water in the wet gas is measured.

15. The system of claim 14, wherein the data associated with the permittivity of the wet gas is obtained using a microwave measurement device.

16. The system of claim 14, wherein the data associated with the amount of water in the wet gas is obtained using a microwave measurement device.

17. The system of claim 14, wherein the data associated with the permittivity of the wet gas is obtained using load-pulled frequency measurement.

18. The system of claim 14, wherein the data associated with the amount of water in the wet gas is obtained using load-pulled frequency measurement.

19. The system of claim 14, wherein the hydrophilic material is an alumina.

20. The system of claim 14, wherein the characteristic measured by the first probe is an electrical characteristic.

21. A method of characterizing constituents of a wet gas, comprising:
    taking measurements to characterize an overall permittivity of the wet gas;
    taking measurements to characterize an amount of water in the wet gas;
    characterizing permittivity of at least one constituent of the wet gas; and
    calculating a percentage of petrol in the wet gas.

22. The method of claim 21, wherein the wet gas comprises oil, a gas, and water.

23. The method of claim 21, wherein the step of taking measurements to characterize an overall permittivity of the wet gas is performed at a first measurement stage that includes a microwave source and detector.

24. The method of claim 21, wherein the step of taking measurements to characterize an overall permittivity of the wet gas is performed at a first measurement stage that includes a densitometer.

25. The method of claim 21, wherein the step of taking measurements to characterize an overall permittivity of the wet gas is performed at a first measurement stage that includes a wet gas flow meter.

26. The method of claim 21, wherein the step of taking measurements to characterize an overall permittivity of the wet gas is performed at a first measurement stage selected from the group consisting of orifice meter, Venturi meter, vortex meter, turbine meter, and V-Cone meter.

27. The method of claim 21, wherein the step of taking measurements to characterize an amount of water in the wet gas is performed at a second measurement stage that includes a microwave source and detector.

28. The method of claim 21, wherein the step of taking measurements to characterize an overall permittivity of the wet gas is performed at a first measurement stage that uses load-pulled frequency measurement.

29. The method of claim 21, wherein the step of taking measurements to characterize an amount of water in the wet gas is performed at a second measurement stage that uses load-pulled frequency measurement.

* * * * *